(12) United States Patent
Yoshitake et al.

(10) Patent No.: US 8,121,398 B2
(45) Date of Patent: Feb. 21, 2012

(54) METHOD AND APPARATUS FOR INSPECTING DEFECTS

(75) Inventors: Yasuhiro Yoshitake, Yokohama (JP); Hiroyuki Nakano, Mito (JP); Yukihiro Shibata, Fujisawa (JP)

(73) Assignee: Hitachi High-Technologies Corporation, Tokyo (JP)

( * ) Notice: Subject to any disclaimer, the term of this patent is extended or adjusted under 35 U.S.C. 154(b) by 394 days.

(21) Appl. No.: 12/420,932

(22) Filed: Apr. 9, 2009

(65) Prior Publication Data

US 2009/0257647 A1 Oct. 15, 2009

(30) Foreign Application Priority Data

Apr. 9, 2008 (JP) ................................. 2008-101338

(51) Int. Cl.
*G06K 9/00* (2006.01)
*H04N 5/335* (2011.01)
(52) U.S. Cl. ..................... 382/149; 356/237.1; 348/308; 382/154
(58) Field of Classification Search .......... 382/145–154, 382/199, 203, 285, 286; 348/308, 86–87, 348/126; 356/237.1–237.5
See application file for complete search history.

(56) References Cited

U.S. PATENT DOCUMENTS

| 5,850,289 | A * | 12/1998 | Fowler et al. ................. 356/603 |
| 6,064,759 | A * | 5/2000 | Buckley et al. ............... 382/154 |
| 6,870,609 | B2 * | 3/2005 | Watkins et al. ............ 356/237.1 |
| 2002/0093585 | A1 * | 7/2002 | Lemstrom et al. ............ 348/374 |
| 2007/0285665 | A1 * | 12/2007 | Shimoda ....................... 356/430 |
| 2010/0104173 | A1 * | 4/2010 | Yoshida et al. ............... 382/145 |
| 2010/0271628 | A1 * | 10/2010 | Nakano et al. ............. 356/237.4 |
| 2011/0141463 | A1 * | 6/2011 | Chikamatsu et al. ....... 356/237.5 |

FOREIGN PATENT DOCUMENTS

| JP | 09-128540 | 5/1997 |
| JP | 09-210917 | 8/1997 |
| JP | 09-264728 | 10/1997 |
| JP | 2003-084444 | 3/2003 |
| JP | 2005-520123 | 7/2005 |
| JP | 2005-294521 | 10/2005 |
| WO | WO 03/001189 A1 | 6/2001 |

* cited by examiner

*Primary Examiner* — Hoa Pham
(74) *Attorney, Agent, or Firm* — Antonelli, Terry, Stout & Kraus, LLP.

(57) ABSTRACT

A two-dimensional sensor is installed inclining at a predetermined angle to a moving direction of a stage on which an object to be inspected is mounted and, in synchronism with the movement of the stage, a picked up image is rearranged so that there can be obtained an image in high-density sampling with a picture-element size or less of the two-dimensional sensor with respect to a wafer. Thus, interpolation calculation during position alignment becomes unnecessary, and size calculation and classification of a defect can be performed with high accuracy.

22 Claims, 20 Drawing Sheets

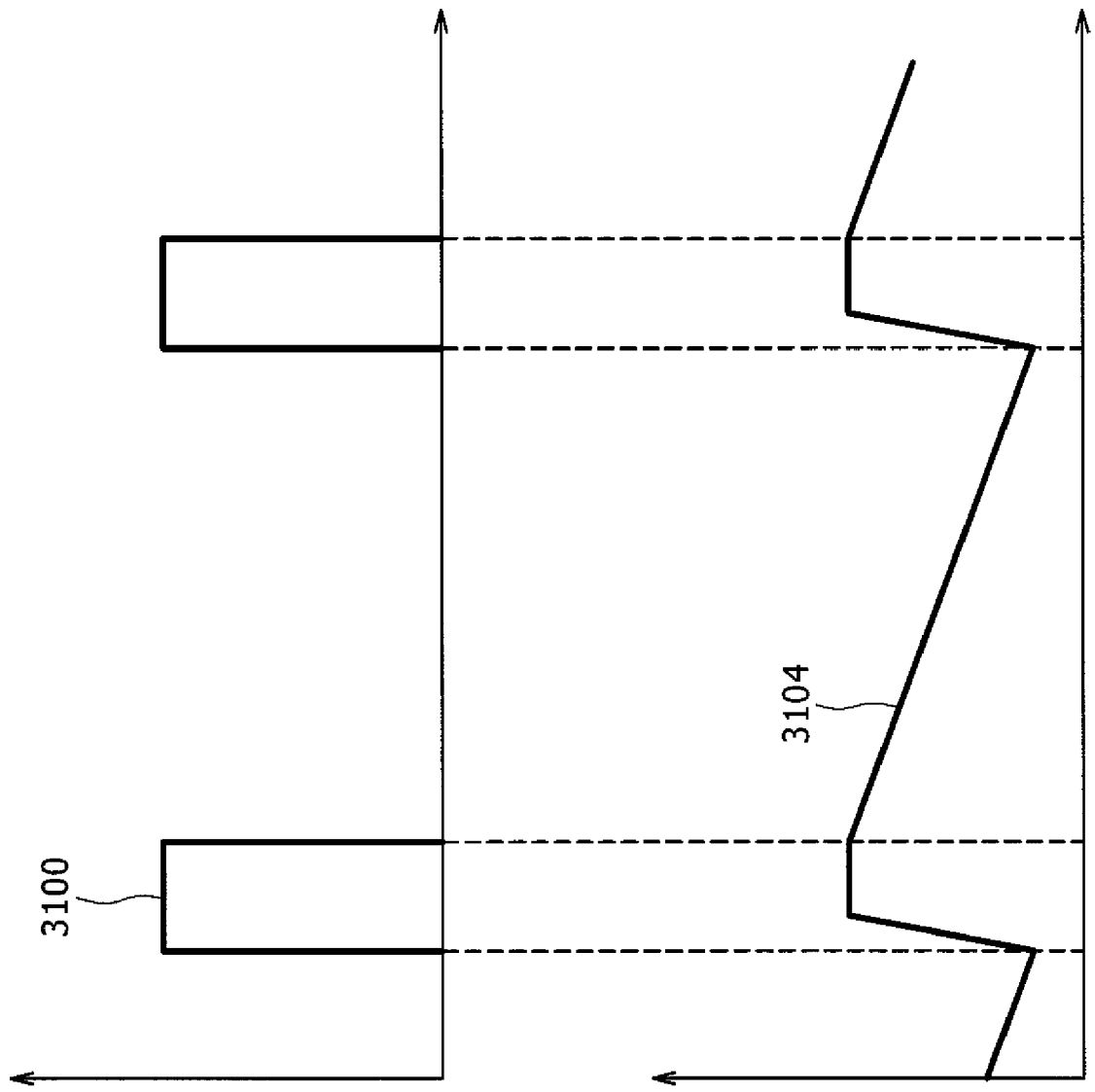

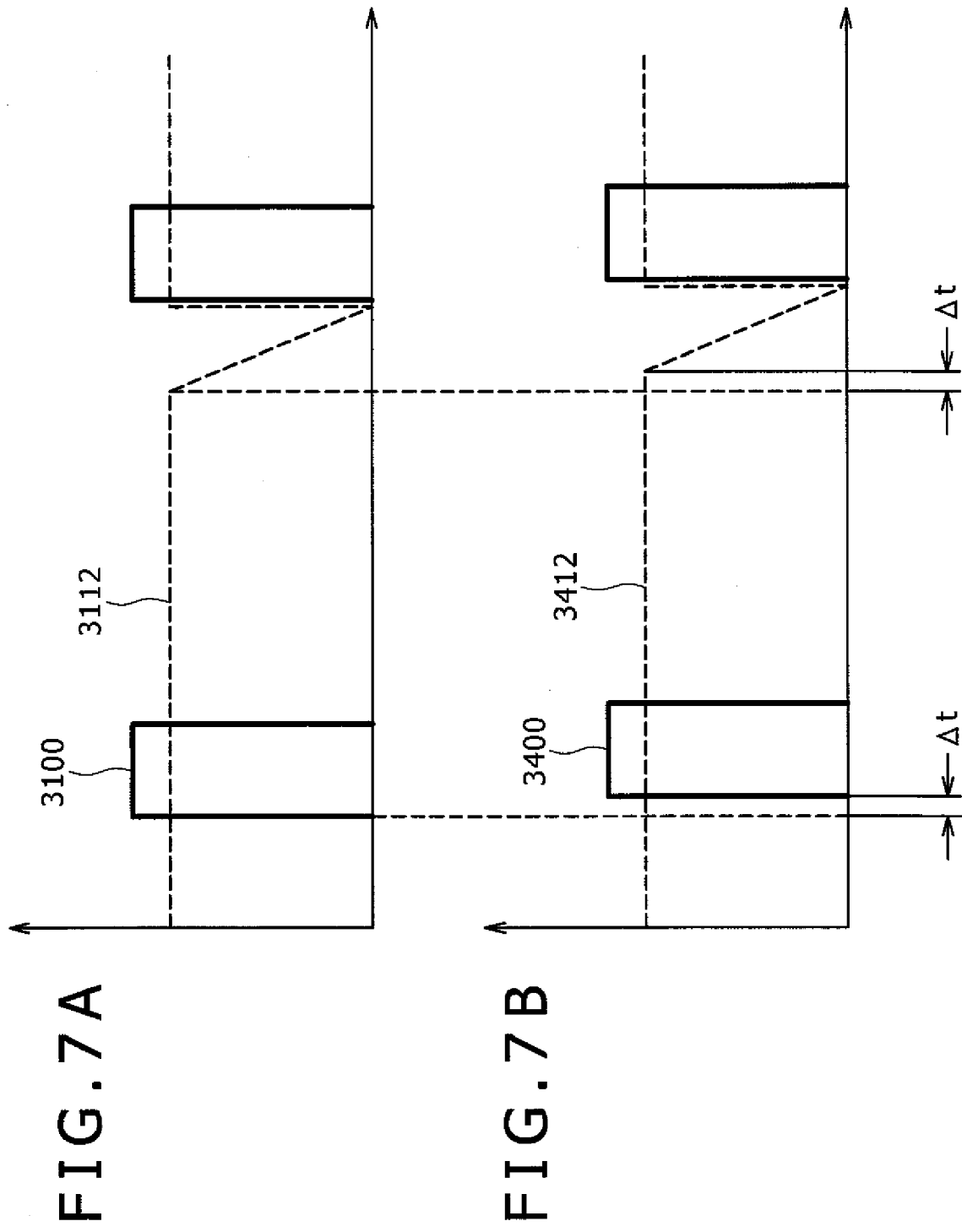

METHOD AND APPARATUS FOR INSPECTING DEFECTS

CLAIM OF PRIORITY

The present application claims priority from Japanese Patent Application JP 2008-101338 filed on Apr. 9, 2008, the content of which is hereby incorporated by reference into this application.

BACKGROUND OF THE INVENTION

The present invention relates to a method and an apparatus for inspecting defects. More specifically, the present invention relates to a method and an apparatus for inspecting defects that measure, at high speed and precision, surfaces of a semiconductor wafer etc. on which many IC chips containing semiconductor circuits therein are formed.

Optical apparatuses are mainly used for inspecting defects of circuit patterns on semiconductor wafers. One such apparatus sequentially picks up images of circuit patterns inside an LSI chip with an image pick-up sensor by scanning a stage on which a wafer is mounted. A circuit-pattern image is compared with a circuit-pattern image of an adjacent chip stored temporarily, and a defect is detected by extracting a difference by image processing. Extraction of the difference depends on scanning accuracy of the stage, and there exists a problem of a shift in position occurring between images of neighboring chips. In order to correct the positional shift of images with one picture element pitch or less of accuracy of the image pick-up sensor, JP-A-9-128540 discloses a method, for example, in which a luminance value at a shift position being one picture-element pitch or less is calculated from luminance values of four spots of neighboring picture elements by inner interpolation.

Also, JP-A-9-264728 discloses a method for calculating a size of a defect from a group of picture elements of an extracted difference. Further, JP-A-2005-294521 discloses a method in which classification of defects such as foreign objects on a rear surface, unevenness, etc. is performed from a direction of a luminance gradient of the extracted group of picture elements.

Still further, JP-T-2005-520123 discloses a method in which picture elements in the stage scanning direction are added and a noise of the image is reduced by combining stage scanning with a two-dimensional CMOS sensor and, also, a method in which a color (RGB) image is picked up by using a color strobe light or a color filter.

On the other hand, as an exposure technology for a printed circuit board, JP-A-2003-84444 discloses a method in which a circuit pattern is directly drawn on a substrate without using a mask for projection but by scanning a stage on which the substrate is mounted and with the use of a micro-mirror array element. In this method, by inclining the stage scanning direction and the direction of the micro-mirror array element by a predetermined angle, a drawing position is controlled with an array-element pitch or less of accuracy.

Still further, JP-A-9-210917 discloses a technology in which a noise of scattered light entering a linear sensor from a circuit pattern on a wafer is reduced by inclining a direction of the wafer at a predetermined angle to the linear sensor and the stage-scanning direction.

As described above, position correction of the image takes time because interpolation calculation of luminance values is necessary from the neighboring picture elements. Further, since linear interpolation is adopted, when the size of the picture element is large with respect to non-linear luminance change, the interpolated luminance value has an error with respect to a luminance value of an actual sample. In this regard, in extracting a defect based on a difference from an adjacent image, there may take place false detection or failing in detecting the defect. On the other hand, also in calculating a size of a defect and classifying defects, calculation can only be carried out by sampling points determined by a size of the picture element with respect to an actual size or shape. Therefore, there is a limit for accuracy in the size and classification.

These problems can be solved by reducing the picture element in size and increasing magnifying power for image pick-up to reduce an area to be inspected on a sample. However, since an image pick-up field becomes smaller, when inspecting a wafer or an entire substrate, the number of reciprocating motions of the stage increases, lowering an inspection throughput.

SUMMARY OF THE INVENTION

The present invention relates to a method and an apparatus for inspecting defects which achieve correction of a position shift smaller than a size of a picture element of an image without lowering an inspection throughput and achieve calculation of the defect size and classification with high accuracy.

That is, according to the present invention, in a defect inspection apparatus which picks up an image by synchronizing the stage on which a sample is mounted with an image sensor, with the use of a two-dimensional sensor as an image sensor, a stage scanning direction and a vertical array direction of the two-dimensional sensor are arranged such that they form a predetermined angle. Also, by inclining the two-dimensional sensor, the time for the stage to pass each picture element in the horizontal array direction is delayed. Therefore, there is provided a delay circuit which delays timing for exposure and reading out of picture elements in the horizontal direction, with respect to neighboring picture elements, by predetermined time periods, respectively.

Also, with respect to picture elements in the vertical array direction, namely, in the stage scanning direction, timing of exposure and reading are synchronized in correspondence to the stage scanning position. Further, simultaneous reading in parallel is achieved by providing, for each picture element, an A/D conversion circuit which converts electric charges accumulated in each picture element to digital values. Still further, there is provided a buffer for storing a light intensity value of each picture element. Still further, there is provided an image generation unit which rearranges luminance values of respective picture elements and forms an image in sampling with a size of one picture element or less.

According to the present invention, an image is picked up in sampling with the size of a picture element or less. Therefore, when calculating a difference image for defect extraction, image interpolation is not necessary, achieving faster defect extraction processing. Also, it becomes possible to calculate a defect size with the size of picture elements constituting the defect or less of accuracy. Further, information about the position of picture elements constituting the defect and luminance values increases. Therefore, feature quantities for defect classification increase, leading to improvement of accuracy of the defect classification.

As a result of the above, an inspection throughput of the defect improves and accuracy of the defect size and classification improves, which brings about the effect of being able to specify the cause of the occurrence of the defect faster and to achieve a high-yield production of semiconductor devices.

These and other objects, features and advantages of the invention will be apparent from the following more particular description of preferred embodiments of the invention, as illustrated in the accompanying drawings.

BRIEF DESCRIPTION OF THE DRAWINGS

FIG. 5A is a graph showing a transitional change of a reset signal 3100 and FIG. 5B is a graph showing a transitional change of a potential 3104 by electric charges of a photodiode 3103;

FIG. 7A shows a reset signal 3100 and an A/D-conversion drive signal 3112 of a picture element 301, and FIG. 7B shows a reset signal 3400 and an A/D-conversion drive signal 3412 of a picture element 302;

DESCRIPTION OF THE PREFERRED EMBODIMENTS

In a defect inspection apparatus which synchronizes a stage on which a sample is mounted with an image pick-up sensor to pick up an image, a two-dimensional sensor is used as an image pick-up sensor, and a stage scanning direction is set to differ from the vertical direction of the two-dimensional sensor by angle α. The two-dimensional sensor includes: an A/D converter for reading a luminance value of each picture element in the stage scanning direction; a buffer in which the luminance value is temporarily stored; and an image generation unit which generates an image in sampling with the size of the picture element or less by rearranging picture elements.

Now, embodiments of the present invention will be described with reference to the drawings.

First Embodiment

Figure 1:
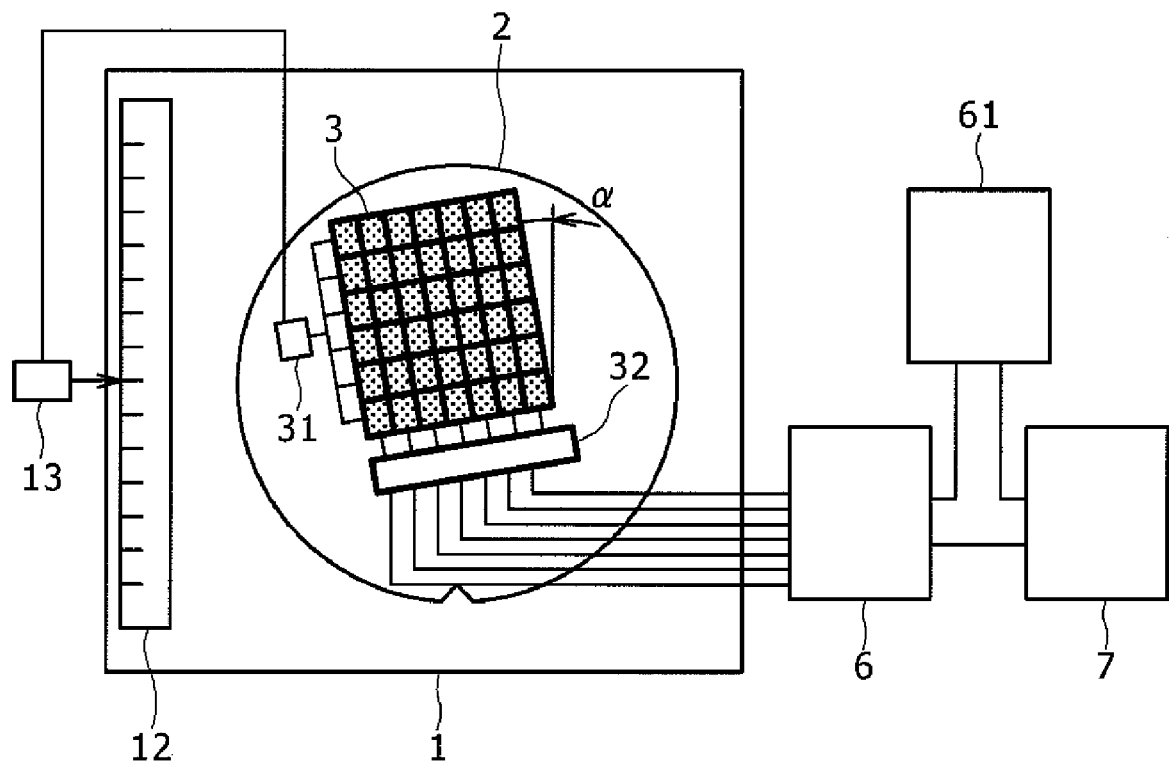
FIG. 1 is a plan view of an inspection apparatus of a slant two-dimensional sensor type of the present invention.
Figure 2:
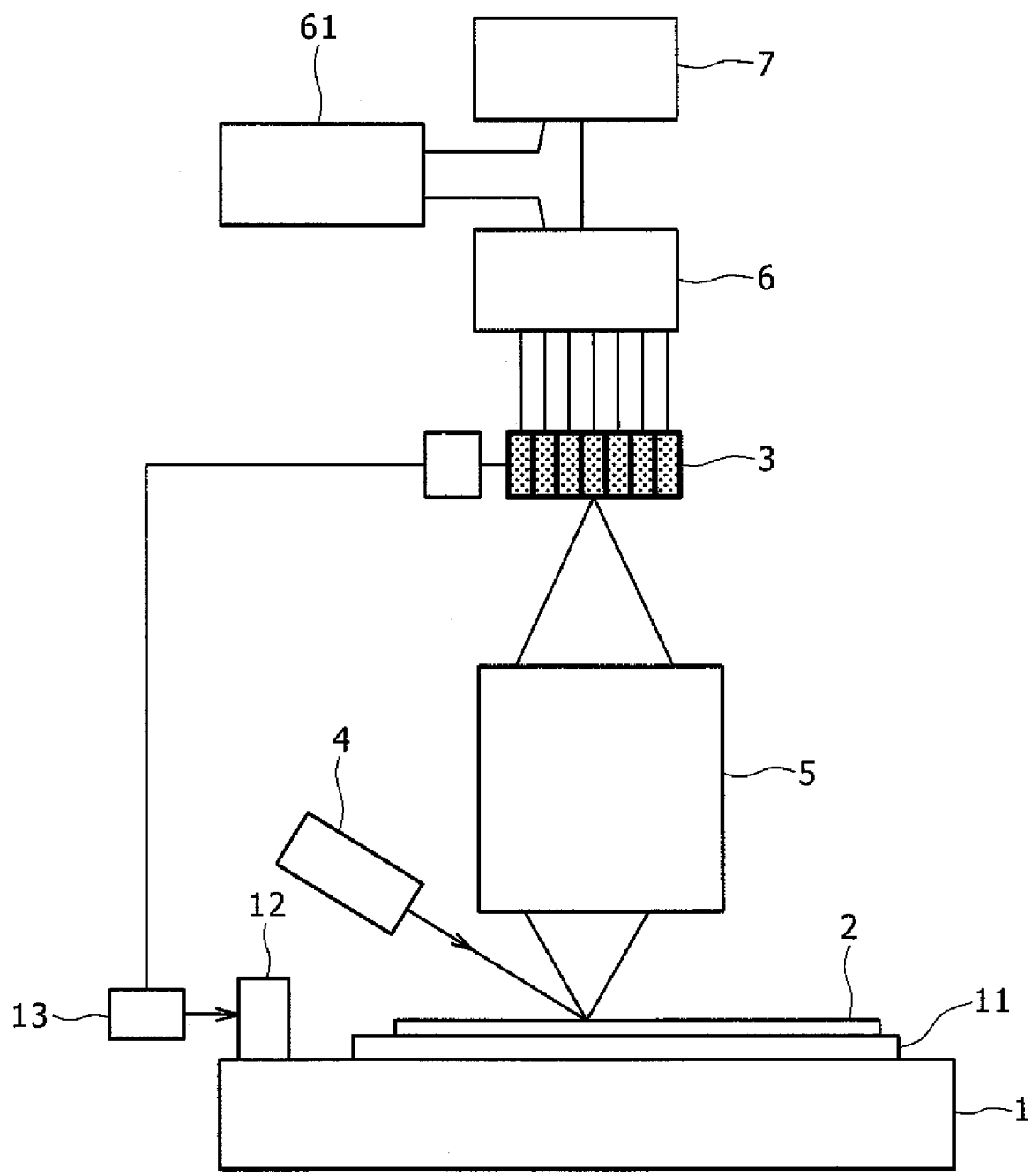
FIG. 2 is an elevation of an inspection apparatus of a slant two-dimensional sensor type of the present invention.

A first embodiment of the present invention will be described with reference to FIGS. 1 to 12. FIG. 1 is a plan of an overall structure of the present embodiment and FIG. 2 is an elevation thereof. A wafer 2 is mounted on a stage 1 through a wafer chuck 11. A scale 12 is provided on the stage 1 and its position is read by a coordinate sensor 13. A two-dimensional sensor 3 is installed inclining with respect to a moving direction of the stage 1 by angle α. A CMOS sensor is used as an image pick-up element of the two-dimensional sensor. The CMOS sensor is suitable as a sensor in the present invention because it can access picked-up image data at random.

An illuminating system 4 irradiates a wafer 2 with light, and an objective lens 5 forms an image of an area of the wafer 2 irradiated by the illuminating system 4 on the two-dimensional sensor 3. Thereby, an image of a defect on the wafer 2 is picked up by the two-dimensional sensor 3. Moreover, a signal of the coordinate sensor 13 is sent to a two-dimensional sensor drive circuit 31. A signal outputted from the two-dimensional sensor 3 is once held in a buffer 32, sent to an image generation unit 6, and is generated as an image. The image is once stored in an image memory 61. Using this image as a reference image, a defect extraction unit 7 aligns it with a newly generated defect image and calculates a difference image to extract a defect.

Figure 3:
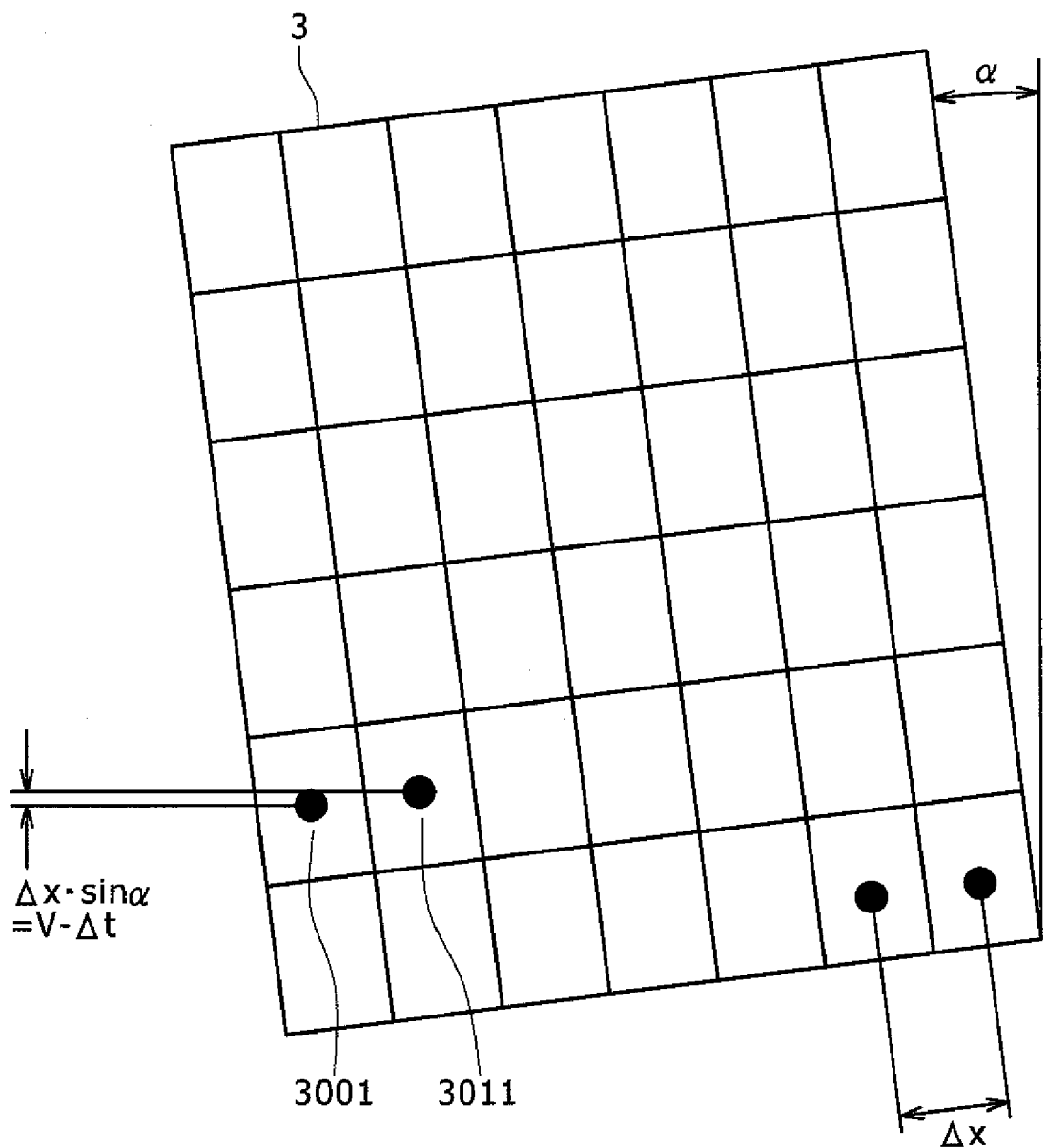
FIG. 3 shows an inclination angle of the two-dimensional sensor 3 and a horizontal pitch of the present invention.

Next, with reference to FIG. 3, the relationship between an array of picture elements of the two-dimensional sensor 3 and the stage moving direction will be described. The two-dimensional sensor 3 is installed inclining at angle α to the moving direction of the stage 1. At this time, assuming a horizontal picture-element pitch is ΔX, a picture-element center 3011 of neighboring picture elements in the horizontal direction is arranged such that it is offset to the moving direction of the stage 1 by $\Delta X \cdot \sin \alpha$ with respect to a picture-element center 3001. Therefore, assuming that the moving speed of the stage is V, the time for the stage 1 to pass the picture-element center 3011 is delayed by $\Delta X \cdot \sin \alpha / V$ with respect to the picture-element center 3001. Considering this delay, reading of a picture element signal should be delayed.

Next, with reference to FIGS. 4 to 6, an explanation will be given of a circuit configuration of the two-dimensional sensor 3 in consideration of the time lag between the picture elements. The two-dimensional sensor drive circuit 31 includes a reset signal generation circuit 310 and an A/D-conversion drive signal generation circuit 311. Each of the circuits generates a signal in synchronism with a position signal of the coordinate sensor 3 of the stage 1. First, focusing on a picture element 301, an action of a reset signal generated by the reset signal generation circuit 310 will be explained. A transistor 3102 is turned ON by a reset wiring 3101. Then, when a photodiode 3103 is charged, the reset is completed. The signal in this regard will be explained with reference to FIG. 5.

FIG. 5A shows a transitional change of a reset signal 3100, and FIG. 5B shows a transitional change of a potential 3104 by an electric charge of the photodiode 3103. The transistor 3102 is turned ON by a pulse of the reset signal 3100, and the potential 3104 by the electric charge of the photodiode 3103 is charged. Then, when the reset signal 3100 becomes zero and the transistor 3102 is turned OFF, the electric charge is gradually discharged by light irradiation to the photodiode 3103. The change in the potential 3104 by the electric charge is sent to the A/D converter 3110 through a wiring 3106 as a voltage signal.

Figure 4:
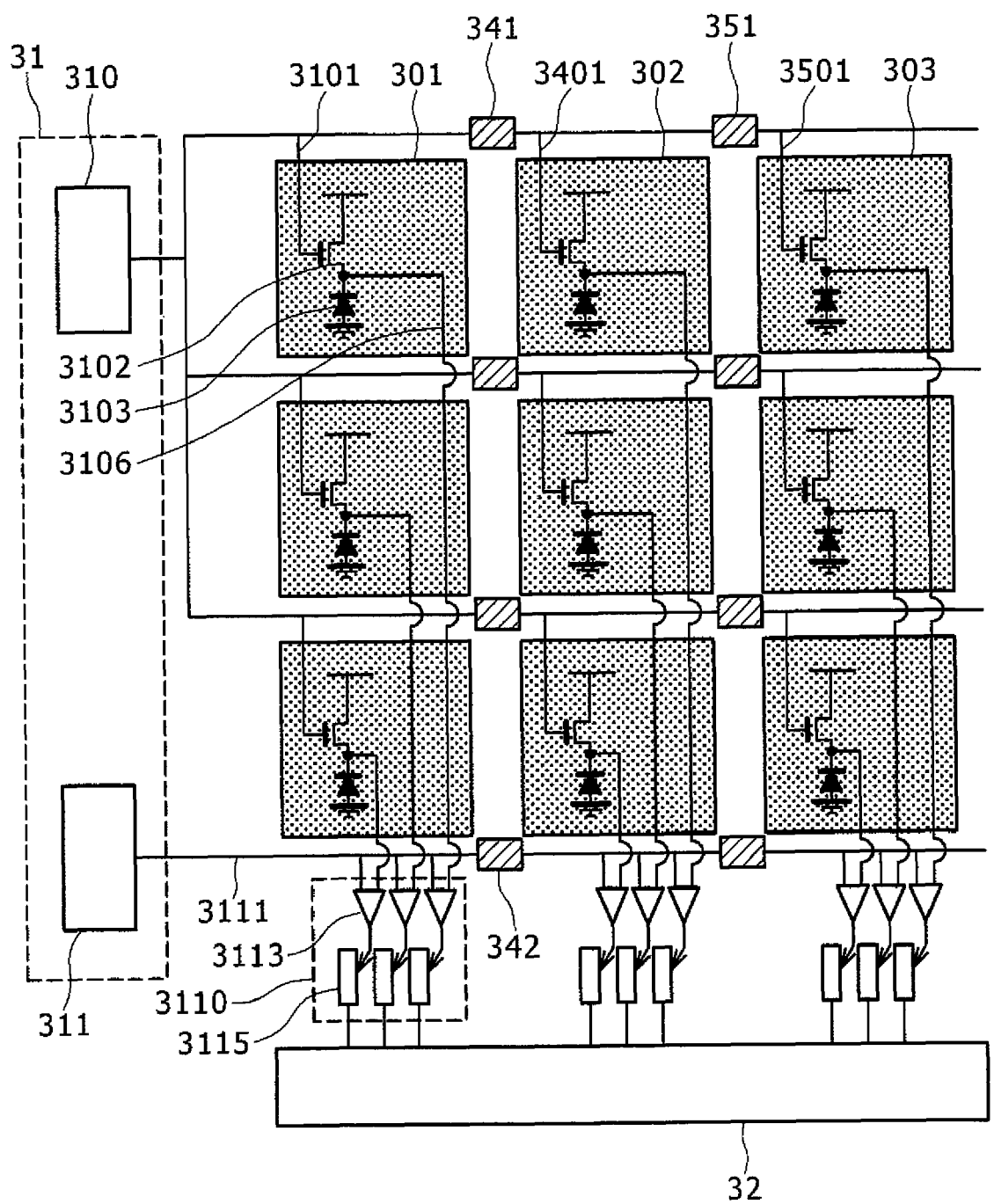
FIG. 4 shows a circuit of the two-dimensional sensor 3 of the present invention.
Figure 6A:
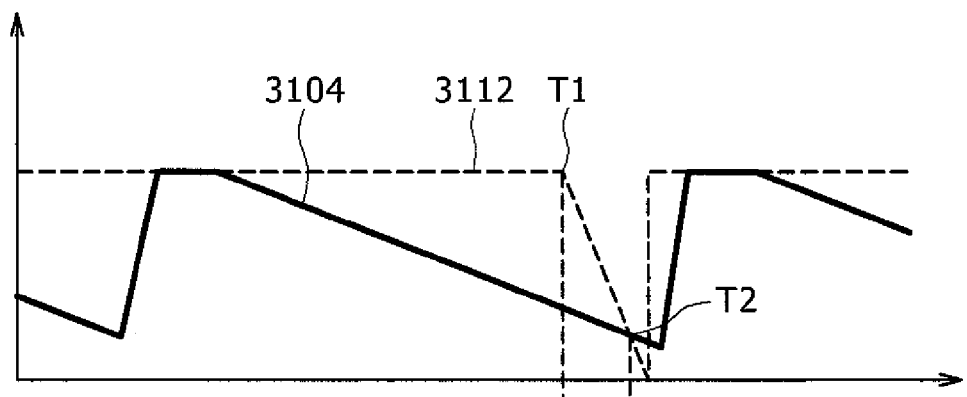
FIG. 6A shows a transitional change of an A/D-conversion drive signal 3112 inputted to a comparator of an A/D converter in which a state is shown where a voltage of a constant value is outputted till time T1 and the voltage is simply decreased after T1.
Figure 6B:
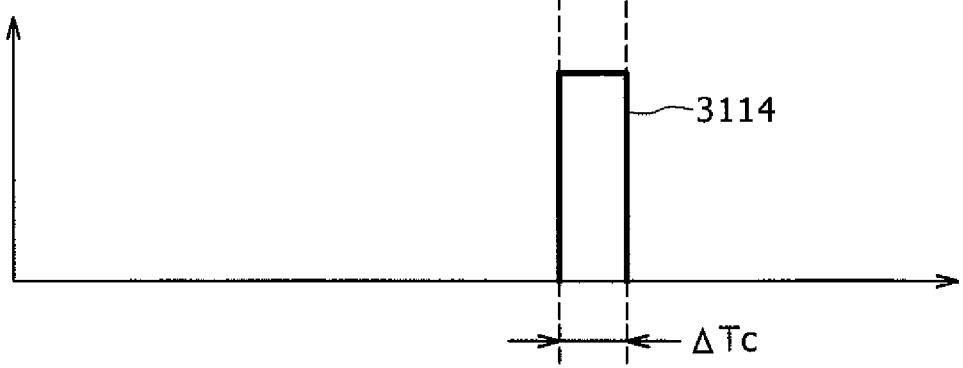
FIG. 6B shows a width ΔTc of a pulse 3114.
Figure 6C:
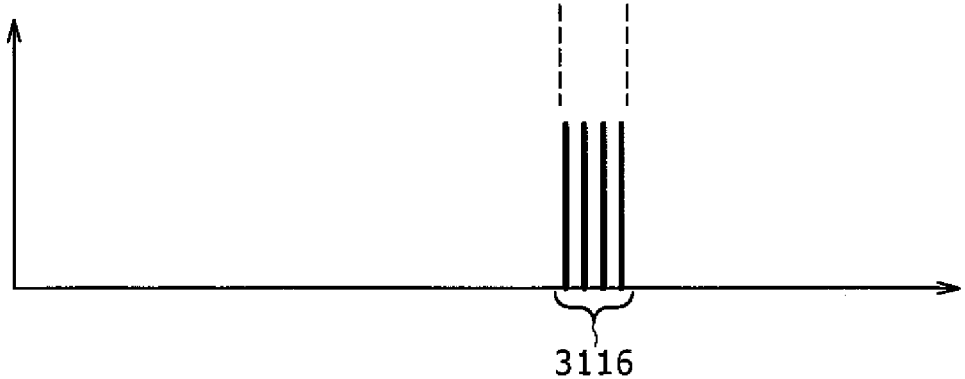
FIG. 6C is a graph showing a state of a pulse 3116 oscillated within the width ΔTc of the pulse 3114.

With reference to FIGS. 4 and 6, an operation of the A/D-conversion drive signal generation circuit 311 will be explained. The A/D-conversion drive signal 3112 of FIG. 6 is inputted through a wiring 3111 of FIG. 4 to a comparator 3113 of the A/D converter 3110. In FIG. 6A, the A/D-conversion drive signal 3112 outputs a voltage of a constant value till time T1. After T1, it outputs a simply decreasing voltage. At T2 in FIG. 6A, a potential 3112 and the potential 3104 become equivalent. After that, the potential 3112 becomes lower than the potential 3104. A width $\Delta Tc$ of a pulse 3114 in FIG. 6B is T2−T1.

The comparator 3113 continues giving output power of "1" until a voltage-converted value of the electric charge 3104 in FIG. 6 and the A/D-conversion drive signal 3112 become equivalent. Therefore, a value of the width $\Delta Tc$ of the output signal 3114 of the comparator 3113 is in proportion to intensity of light irradiated to a picture element 301. In regard to the width $\Delta Tc$ of the output signal 3114, the number of pulses 3116 is counted by the counter 3115 of FIG. 4, and the value obtained is sent to the buffer 32 as a luminance value.

On the other hand, as described above, the time for the stage to pass the neighboring picture elements in the horizontal direction is delayed. Therefore, it is necessary to delay the reading of the light intensity. This operation will be explained with reference to FIGS. 4 and 7. In FIG. 4, a delay circuit 341 is installed on a reset signal line to the neighboring picture element 302 in the horizontal direction. The delay time is set, as described above, such that $\Delta t = \Delta X \cdot \sin \alpha / V$. There is also provided in the A/D-conversion drive signal to a picture element 302 a delay circuit 342 which similarly delays the time by $\Delta t$.

A reset signal and an A/D-conversion drive signal at this time are shown in FIG. 7. FIG. 7A shows the reset signal 3100 of the picture element 301 and the A/D-conversion drive signal 3112, and FIG. 7B shows a reset signal 3400 and an A/D-conversion drive signal 3412 of a picture element 302. The signals of the picture element 302 are delayed by $\Delta t$, respectively. Similarly, in regard to a picture element 303, since a delay circuit 351 is further connected in series, both the reset signal and the A/D-conversion drive signal are delayed by $2 \cdot \Delta t$ with respect to the signal of the picture element 301.

As shown in FIG. 4, in the picture elements in the vertical direction of the two-dimensional sensor 3, the same signals as the ones in the horizontal direction are inputted in parallel. Thereby, in the buffer 32 of FIG. 4, the luminance values of all the picture elements are stored in parallel. FIG. 4 shows an array of picture elements of 3×3. The luminance values of all the picture elements are stored in parallel by nine counters. The luminance values stored in the buffer 32 are sent to the image generation unit 6.

Figure 8:
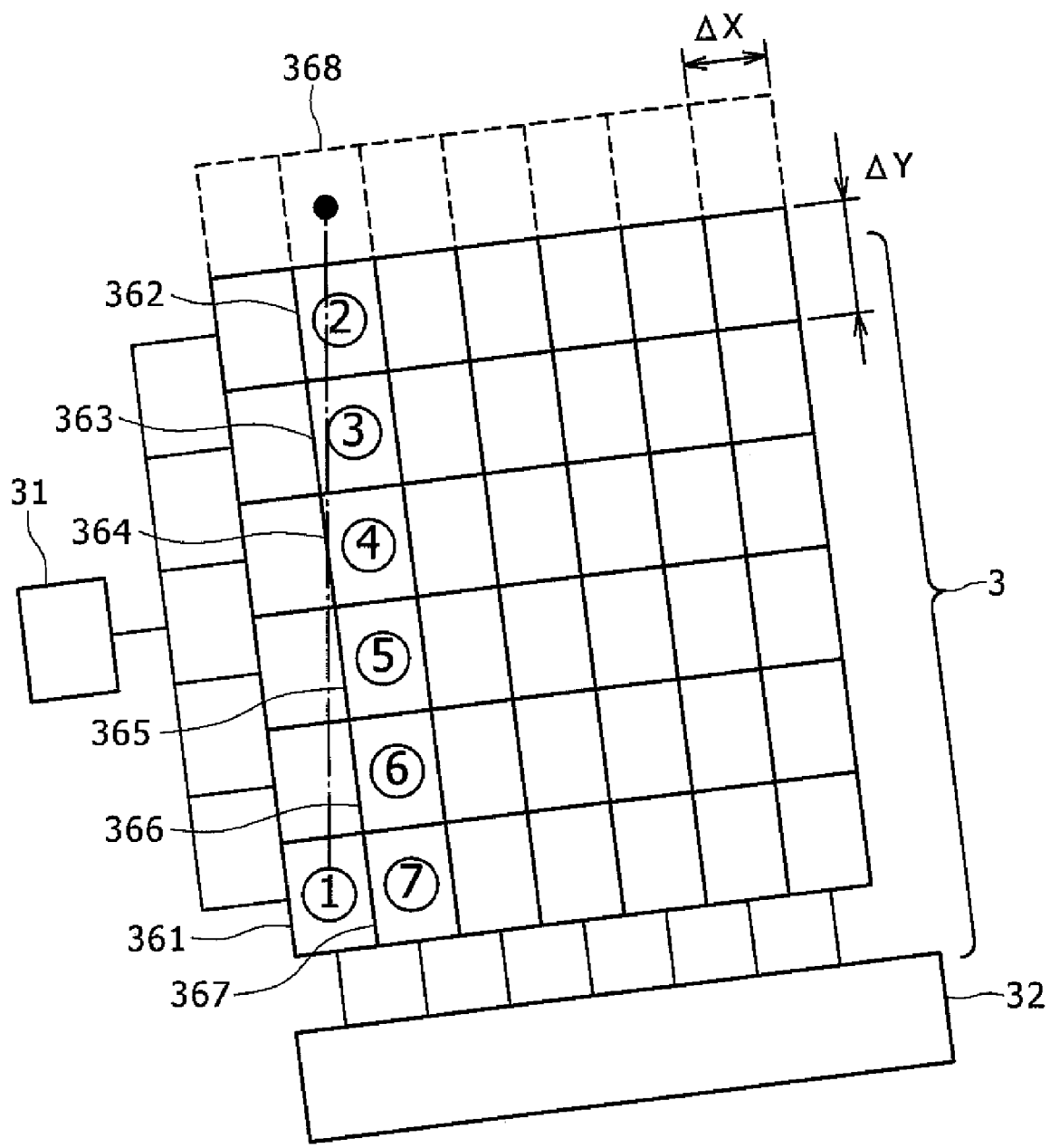
FIG. 8 shows a picture element on the two-dimensional sensor 3 which constitutes an original picture-element pitch in a high-density sampling image which the image generation unit 6 generates.

In this regard, with reference to FIGS. 8 to 11, how the image generation unit 6 generates an image from the luminance value of each picture element of the buffer 32 will be explained. FIG. 8 shows picture elements 361 to 366 which constitute a portion for the picture-element pitch of the two-dimensional sensor 3 in a high-density sampling image which the image generation unit 6 generates. In this regard, assuming that the picture-element pitch in the horizontal direction of the two-dimensional sensor 3 is $\Delta X$, the picture-element pitch in the vertical direction is $\Delta Y$, and an angle formed by the moving direction of the stage 1 and the two-dimensional sensor 3 is $\alpha$, the angle $\alpha$ is set as shown by Expression (1).

$$\tan \alpha = \Delta X / (m \Delta Y) \quad (1)$$

In Expression (1), m is an integer and, in the case of FIG. 8, m=7. A picture element 368 is a vertical picture element. Also, the picture element 368 is on a moving line of the stage 1 with respect to the picture element 361, and is the picture element whose image is picked up at positions in the same horizontal direction with respect to the stage 1. In the present embodiment, the picture element in the seventh line shown by dots is not necessary. Therefore, the picture elements up to the sixth line constitute a portion of one pitch ($\Delta X$) in the horizontal direction of picture elements. Further, a picture element 367 is the one which constitutes a neighboring pitch in the horizontal direction.

Figure 9:
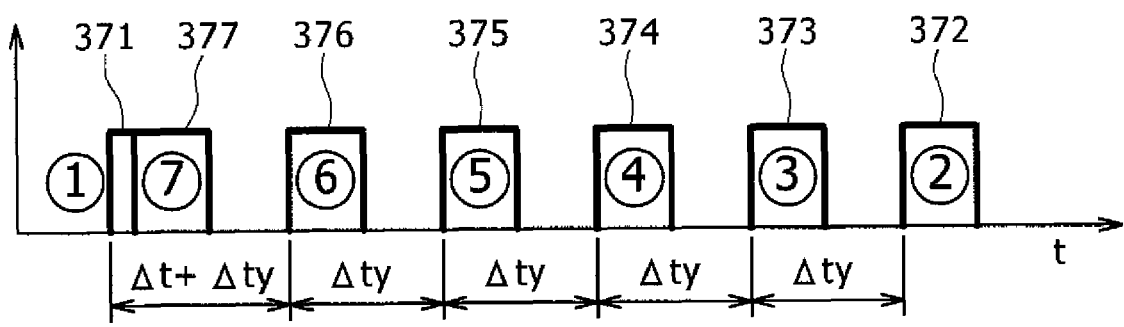
FIG. 9 shows the order of picture elements 361 to 367 of FIG. 8 picking up images in time series.
Figure 10:
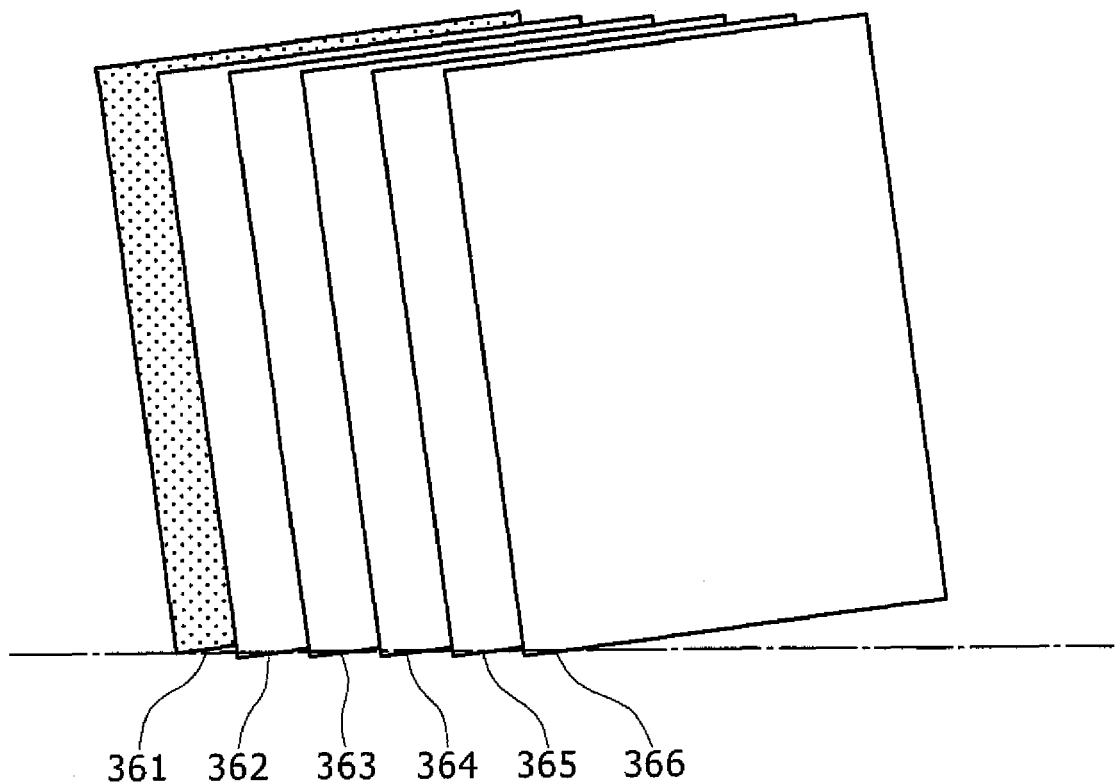
FIG. 10 shows the picture elements 361 to 367 which the image generation unit 6 rearranged.

FIG. 9 shows the order in time series in which luminance values 371 to 377 corresponding to picture elements 361 to 367 are picked up and stored. In this regard, the luminance values 371 to 376 corresponding to the picture elements 361 to 366 constitute a set of data. Also, the luminance value 377 corresponding to the picture element 367 constitutes a set of neighboring data. In FIG. 9, an interval $\Delta ty$ of reset signals for each picture element to pick up images in the wafer moving direction is $\Delta Y \cdot \cos \alpha / V$. However, in FIG. 9, in spite of the interval between the luminance value 376 and the luminance value 365 being $\Delta ty$, the interval between the luminance value 371 and the luminance value 376 is $\Delta ty + \Delta t$. In this regard, $\Delta t = \Delta X \cdot \cos \alpha / V$. This is because the picture element 361 and the picture element 366 exist in different rows.

Figure 11:
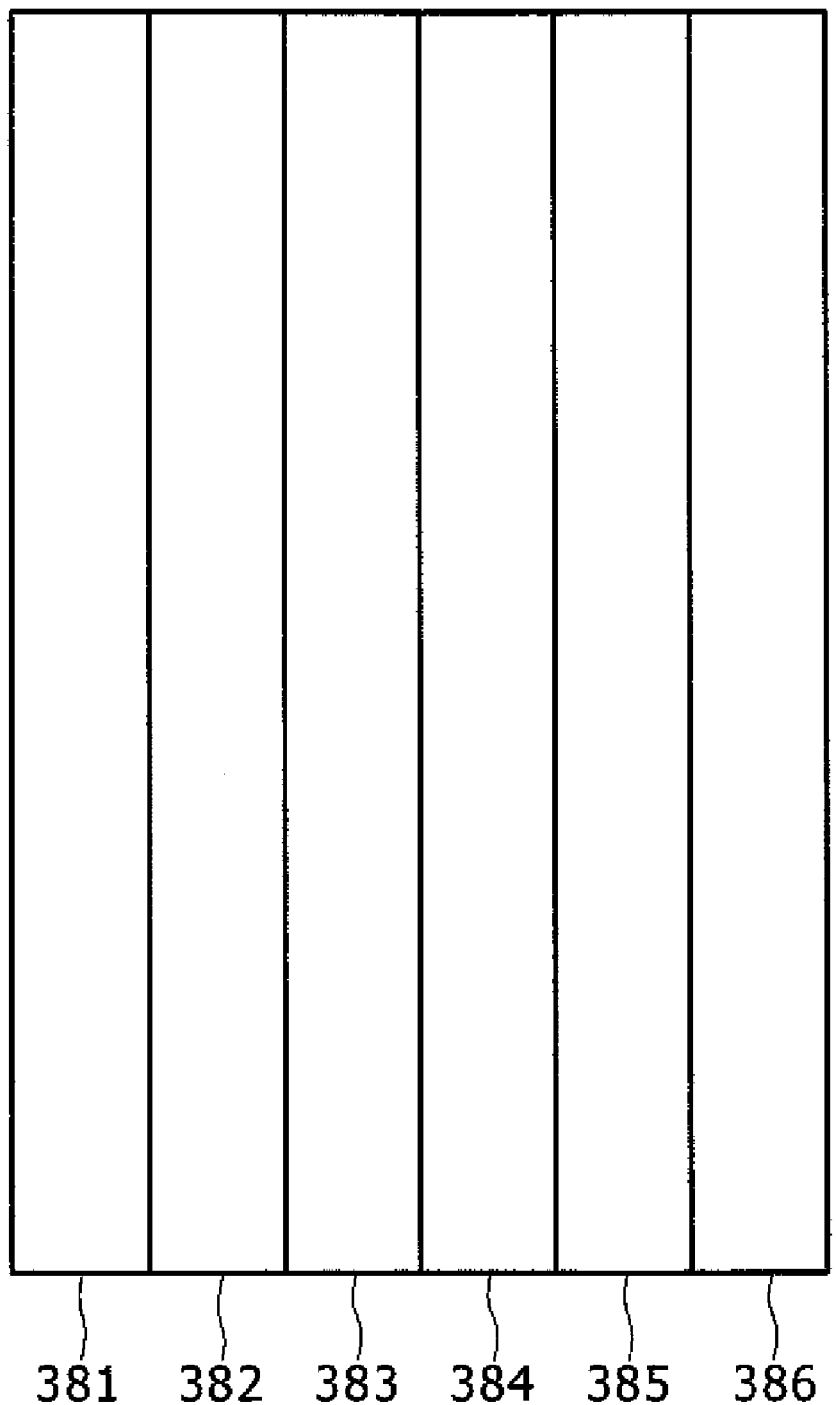
FIG. 11 shows horizontal picture elements in the image after rearrangement.

These luminance values are held in the buffer 32. Like the picture elements 361 to 366 in FIG. 10, the image generation unit 6 rearranges these luminance values 371 to 376 spatially such that they constitute a portion for one pitch in the horizontal direction. The luminance value 377 in FIG. 9 constitutes a neighboring pitch in the horizontal direction. FIG. 11 shows horizontal picture elements 381 to 386 in an image after rearrangement. The picture elements 381 to 386 have luminance values 371 to 376.

Figure 12:
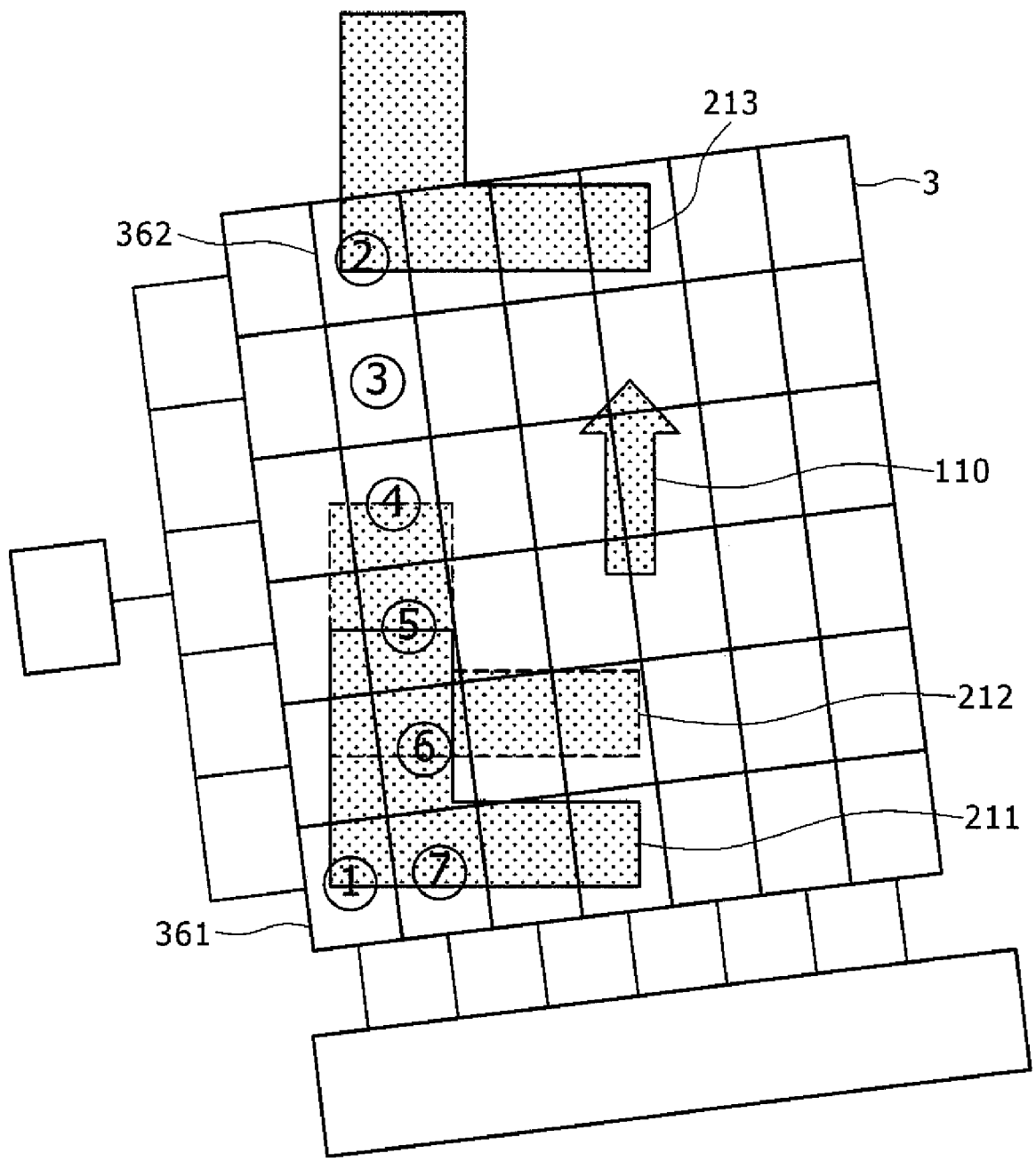
FIG. 12 shows the two-dimensional sensor 3 which performs linear sensor-like image pick-up in synchronism with a stage 1.

In the series of processing, the two-dimensional sensor 3 performs image pick-up, in terms of function, similar to the one that a linear sensor does. FIG. 12 shows how the two-dimensional sensor 3 does it. By means of the stage 1, the wafer 2 moves in a direction 110 forming the angle α with the two-dimensional sensor 3. The picture elements 361, 366, and 362 pick up images at pattern positions 211, 212, and 213, respectively. That is, the picture elements 361 to 366 pick up images in accordance with the movement of the wafer 2.

Figure 13:
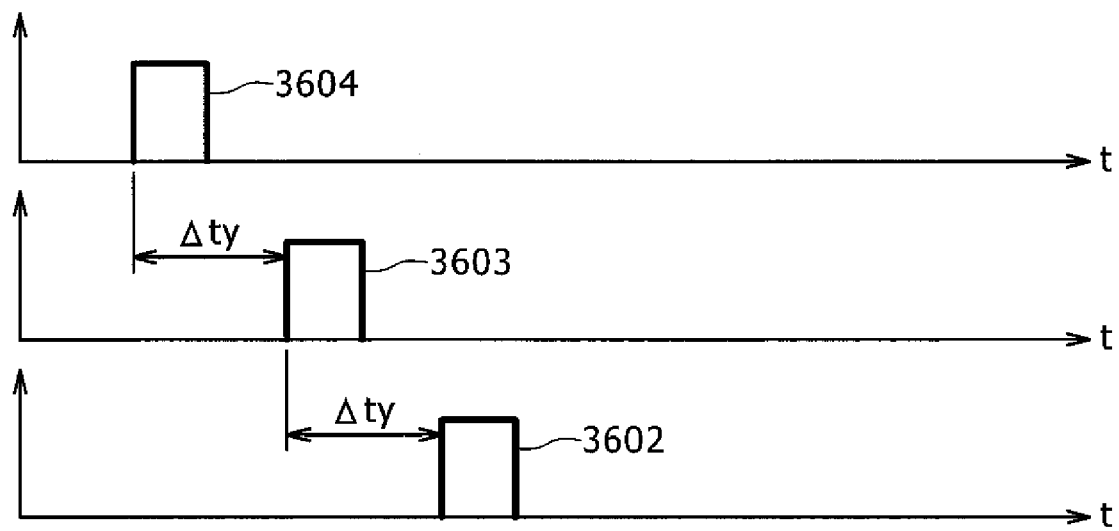
FIG. 13 shows the time-series relationship among the reset signals of the picture elements 361 to 363.

As an example, timing with which the picture elements 364, 363, and 362 pick up images will be shown in FIG. 13. The reset signals of the picture elements 364, 363, and 362 are driven with timing of 3604, 3603, and 3602. These reset signals are generated by the reset signal generation circuit when the coordinate sensor 13 of FIG. 1 detects the time at which the stage 1 reaches each picture element and sends a signal to the reset signal generation circuit 310. The interval Δty of the reset signals is ΔY·cos α/V. Like the reset signal generation circuit 310, the A/D-conversion drive signal generation circuit 311 also generates an A/D-conversion drive signal for each picture element by the start-up of the signal of the coordinate sensor 13.

Figure 14:
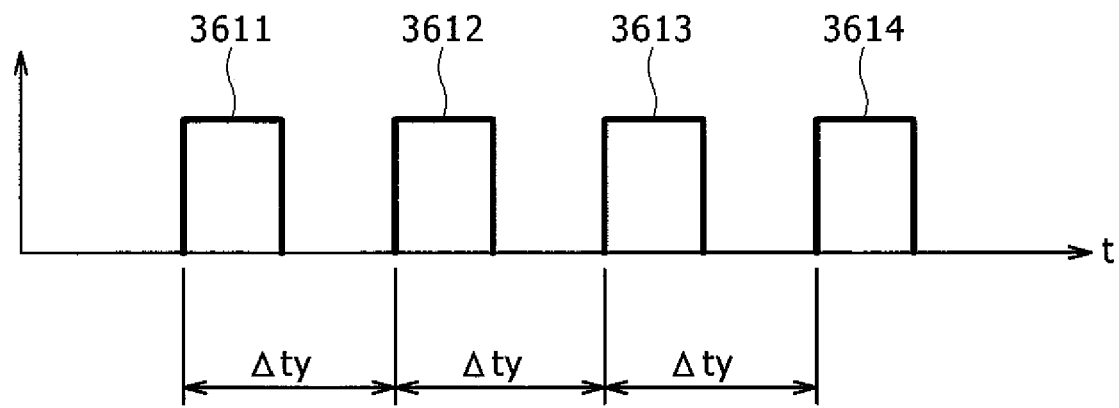
FIG. 14 shows the interval of the reset signals of the picture element 361.
Figure 15:
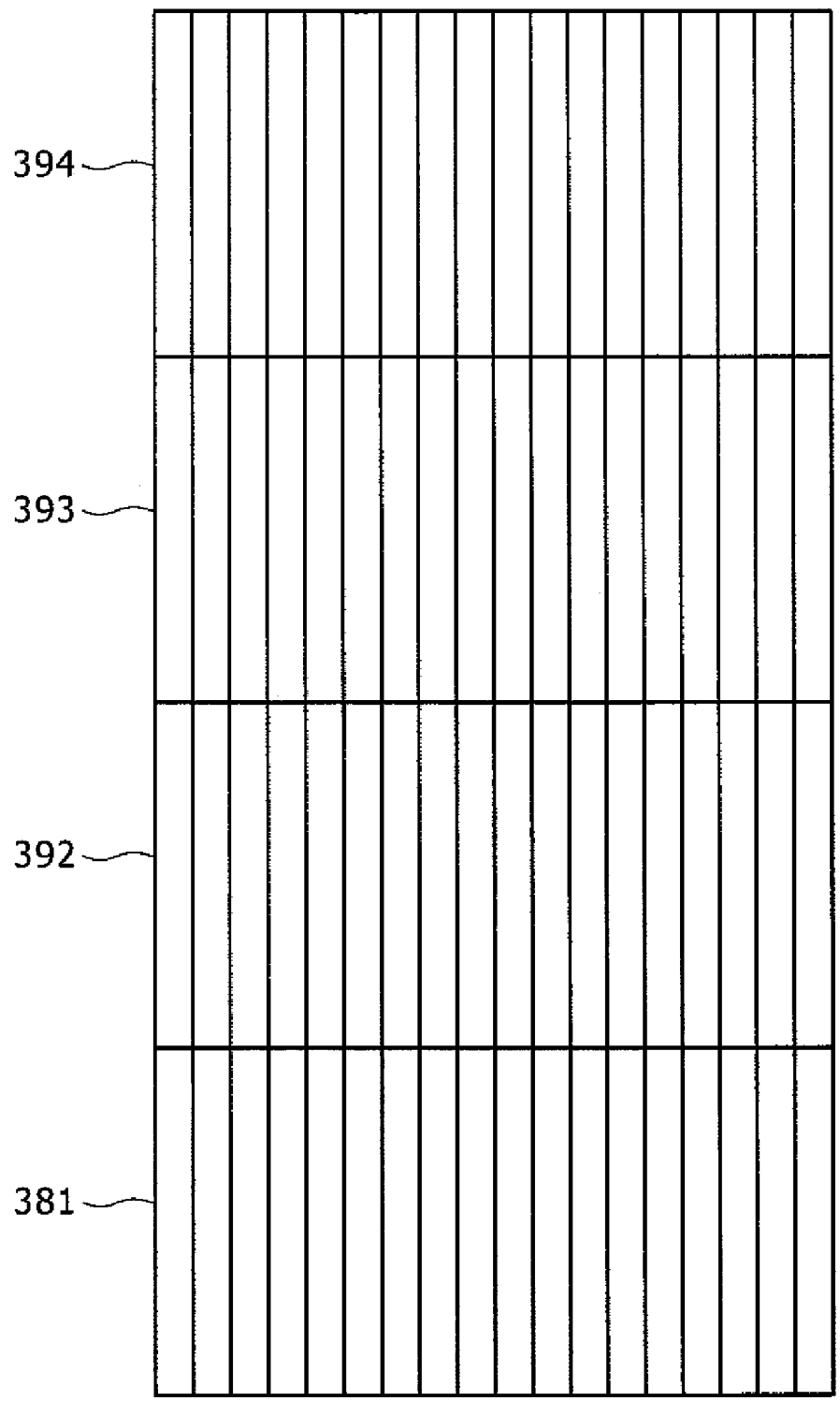
FIG. 15 shows a two-dimensional image which the image generation unit 6 generated.

As above, how to generate a linear horizontal image in the image generation unit 6 by use of vertical picture elements of the two-dimensional sensor 3 has been described. Now, with reference to FIGS. 14 and 15, a method to generate a two-dimensional image from a linear image will be described. FIG. 14 shows reset signals 3611 to 3614 of the picture element 361 in FIG. 12. The interval between reset signals is the above-described Δty. Accordingly, in synchronism with the stage 1 moving by one picture element, images are picked up continuously. By arranging luminance values 381 to 394 picked up with timing of the reset signals 3611 to 3614 in a vertical direction, the image generation unit 6 generates a two-dimensional image of FIG. 15.

Figure 16:
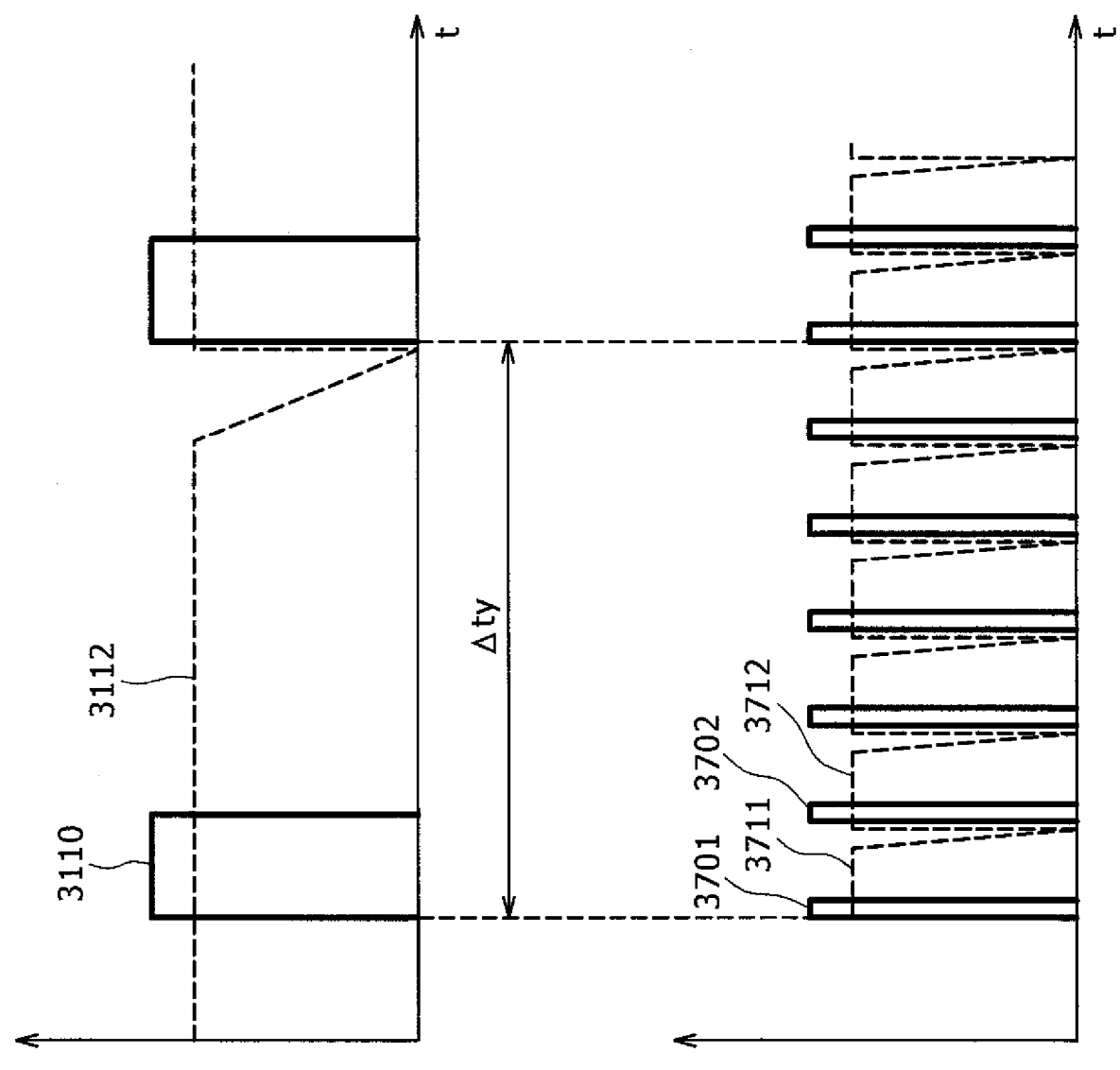
FIG. 16A illustrates how to make an image pick-up pitch smaller in a vertical direction of the two-dimensional sensor 3, showing the relationship between the reset signal 3110 and the A/D-conversion drive signal 3112 and the case where the interval of the reset signals is Δty.
FIG. 16B illustrates how to make an image pick-up pitch smaller in the vertical direction of the two-dimensional sensor 3, showing the relationship between the reset signal 3110 and the A/D-conversion drive signal 3112 and the case where the interval between the reset signals 3701 and 3702 as well as between the A/D-conversion drive signals 3711 and 3712 is Δty/N.

Next, with reference to FIG. 16, how to make an image pick-up pitch smaller in the vertical direction of the two-dimensional sensor 3 will be explained. FIG. 16A shows the reset signal 3110 and the A/D-conversion drive signal 3112 of FIG. 7A. The interval of the reset signals is the above-described Δty. On the other hand, in FIG. 16B, the interval between the reset signal 3701 and the reset signal 3702 as well as between the A/D-conversion drive signal 3711 and the A/D-conversion drive signal 3712 is Δty/N. N is an integer.

Figure 17:
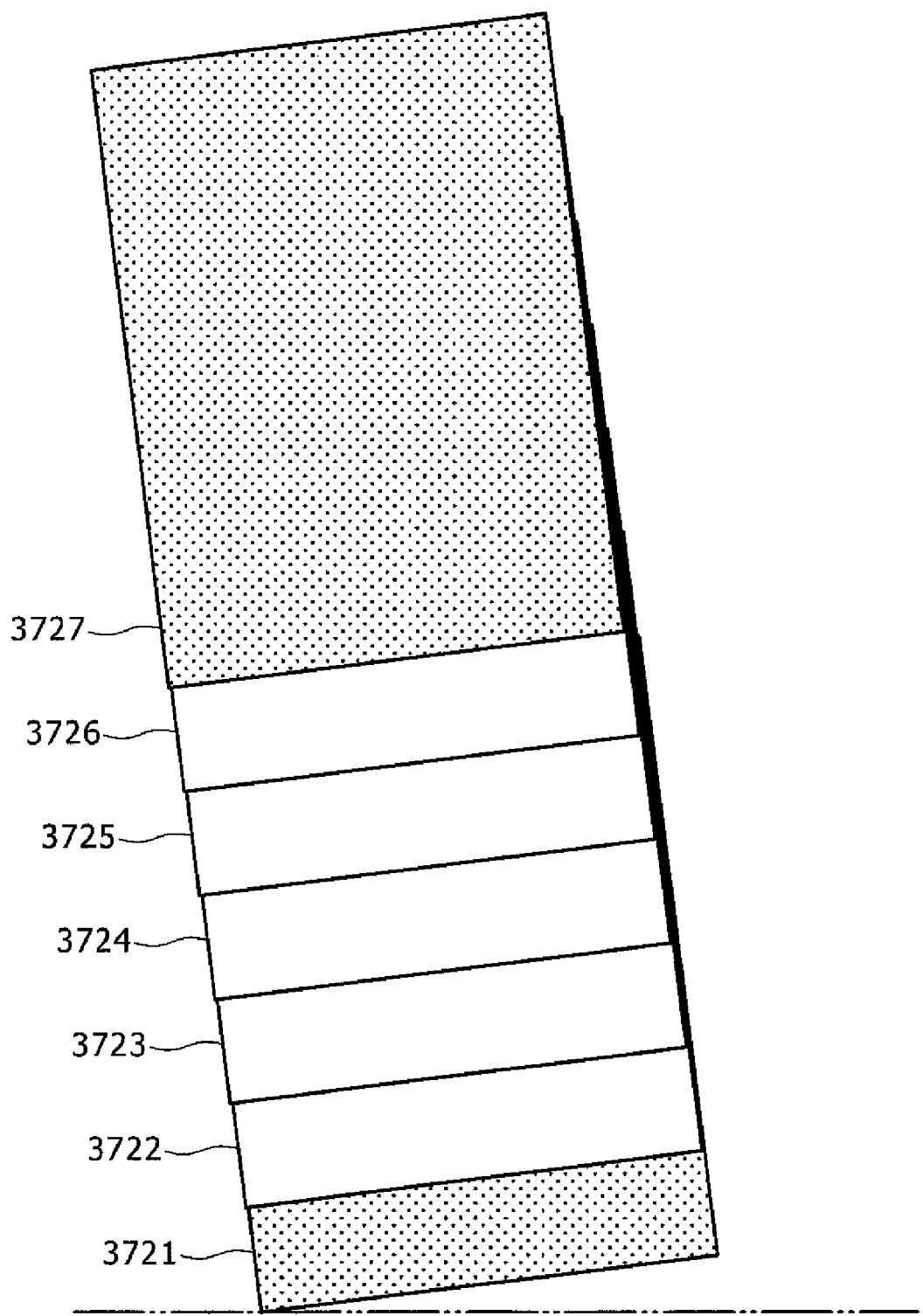
FIG. 17 shows a position of the picture element picked up by the signal of FIG. 16.
Figure 18:
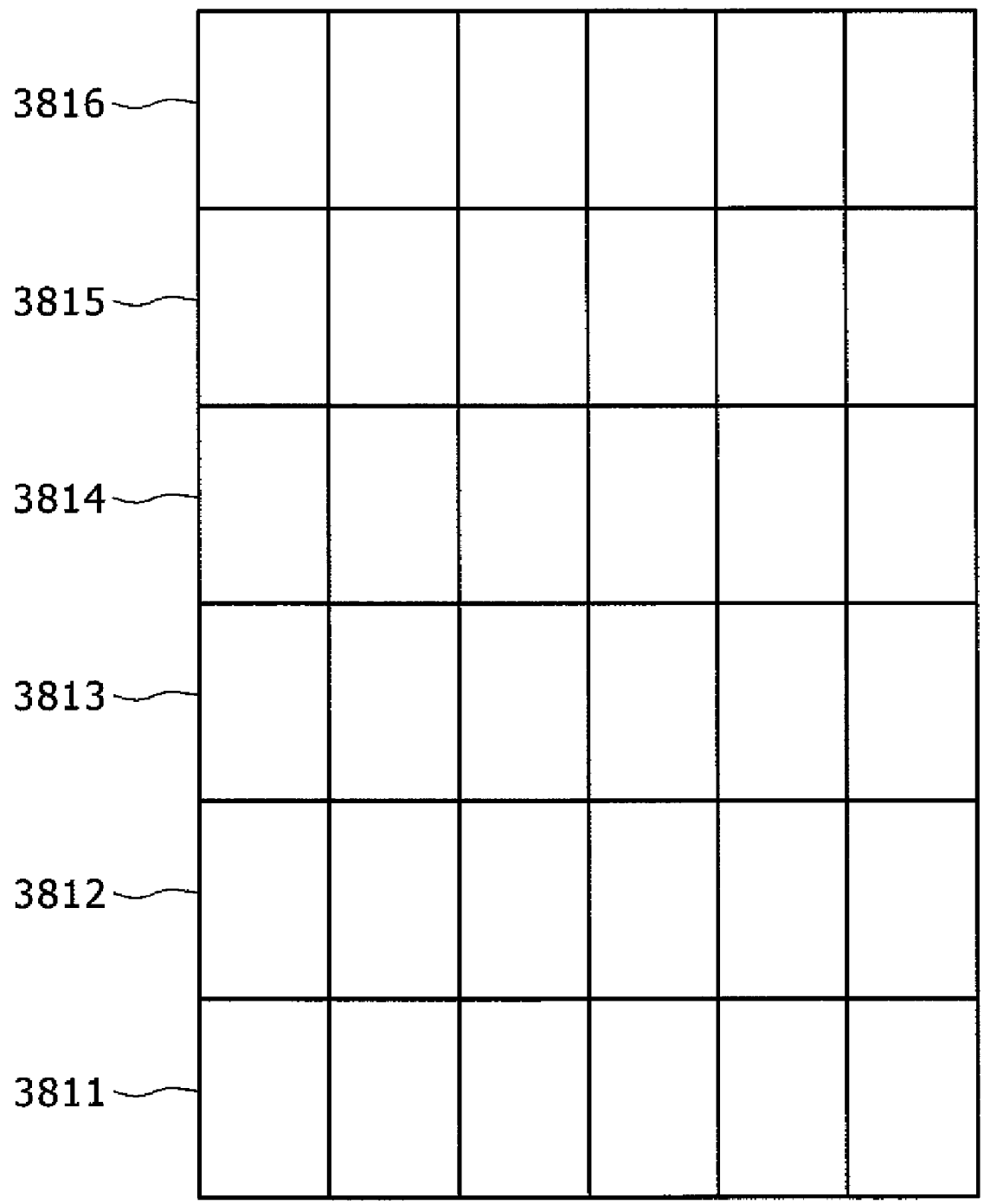
FIG. 18 shows an image in which high-density sampling of the image of FIG. 11 is performed also in the vertical direction.

Thus, by picking up images N times while the stage 1 advances as much as one picture element (ΔY·cos α), the luminance values at positions of the picture elements 3721 to 3726 of FIG. 17 can be picked up. FIG. 17 shows a case where N is 6. FIG. 18 shows an image generated from the image of FIG. 11 by sampling with a pitch of the picture element or less also in the vertical direction. The picture element 381 of FIG. 11 is divided into picture elements 3811 to 3816 in FIG. 18.

Figure 19:
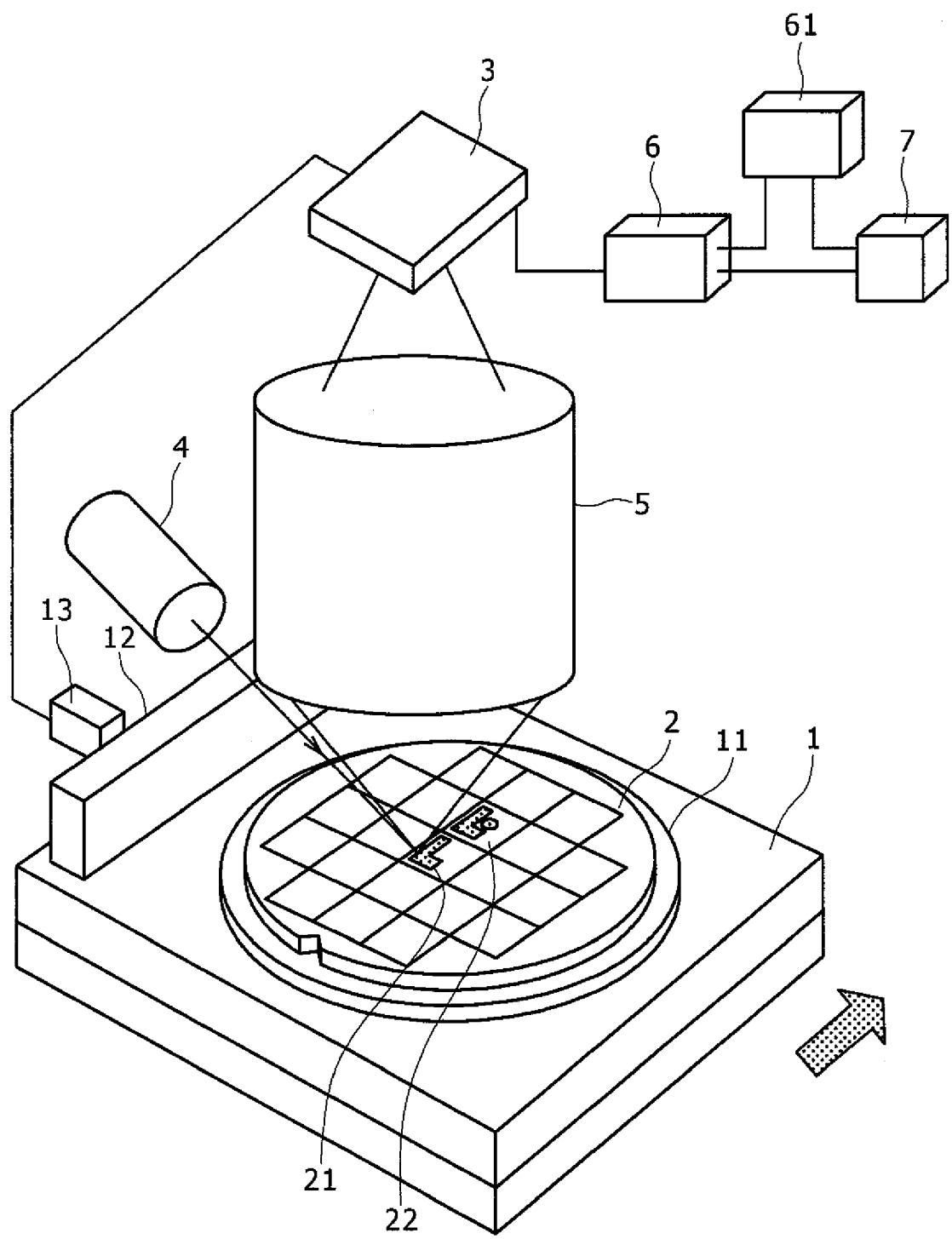
FIG. 19 is a perspective view of an inspection apparatus of a slant two-dimensional sensor type according to the present invention.
Figure 20A:
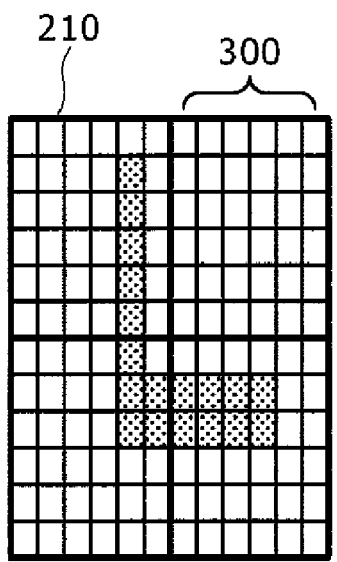
FIG. 20A shows an image 210.
Figure 20B:
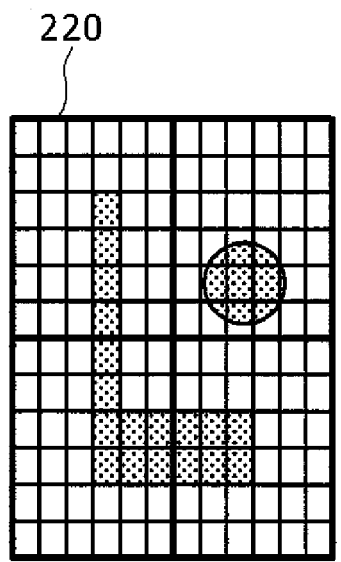
FIG. 20B shows an image 220.
Figure 20C:
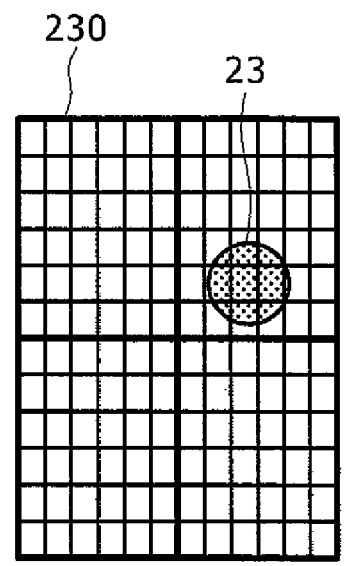
FIG. 20C shows an image 230 which is obtained by aligning the image 210 and the image 220 with a size of the picture element 300 or less of accuracy and calculating the difference.

Finally, with reference to FIGS. 19 and 20A to 20C, an operation of a defect extraction unit 7 will be explained. With use of an image pick-up signal of the two-dimensional sensor 3 in accordance with the movement of the stage 1 of FIG. 19, first, an image of a pattern 21 on the wafer 2 is formed by the image generation unit 6 and is held in an image memory 61. Then, an image of a pattern 22 is picked up and its image is formed. In FIGS. 20A to 20C, the positions of the image 210 of the pattern 21 and the image 220 of the pattern 22 in FIG. 19 are shifted due to an error in movement of the stage 1 and vibration of the objective lens 5 or the two-dimensional sensor 3.

By aligning, with a size of a picture element 300 or less of accuracy, the image 210 of FIG. 20A with the image 220 of FIG. 20B and calculating the difference, the defect extraction unit 7 obtains an image 230 in FIG. 20C. A defect 23 is extracted from the image 230. Also, it becomes possible to calculate the size of the extracted defect 23 with sampling of the size of the picture element 300 or less and further to perform defect classification based on the luminance distribution and shape of the picture elements constituting the defect 23.

Figure 21A:
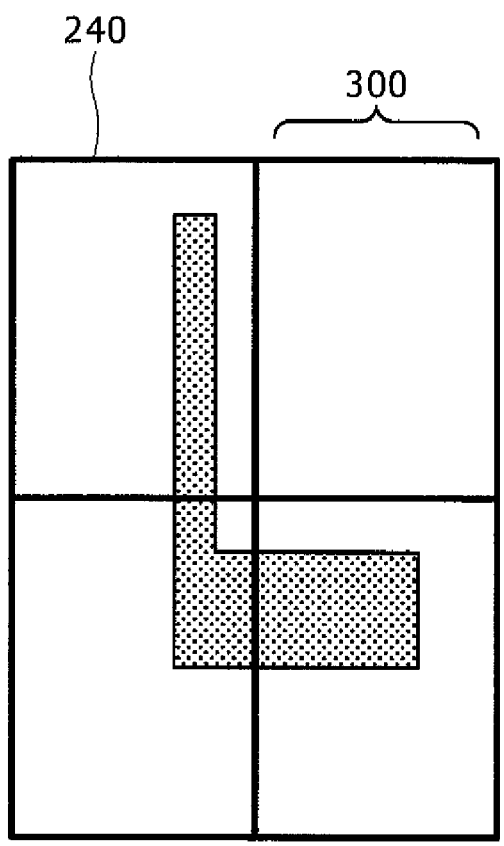
FIG. 21A shows the relationship between a size of a picture element picked up by a conventional image pick-up method and a pattern, and FIG. 21B also shows the relationship between the size of the picture element picked up by the conventional image pick-up method and a pattern containing a defect.
Figure 21B:
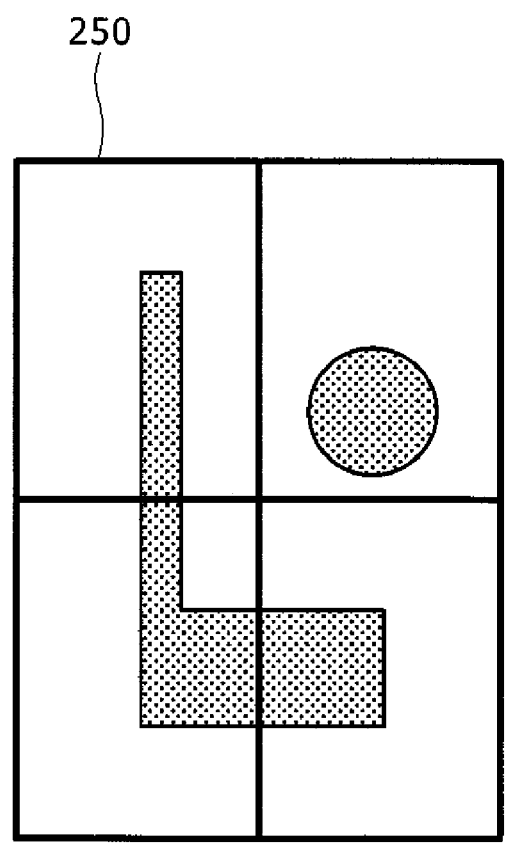

On the other hand, in the conventional image pick-up method, as in FIGS. 21A and 21B, an image is picked up with the size of the picture element 300. Therefore, with respect to both the images 240 and 250, only the luminance information of 2×2 is obtained. Thus, even when using interpolation, since the original information is not enough, it is difficult to perform alignment with high accuracy. Moreover, since the information about one picture element only for the defect 23 is obtained, it is difficult to perform size calculation and defect classification.

(Modification of Two-Dimensional Sensor 3)

Figure 22:
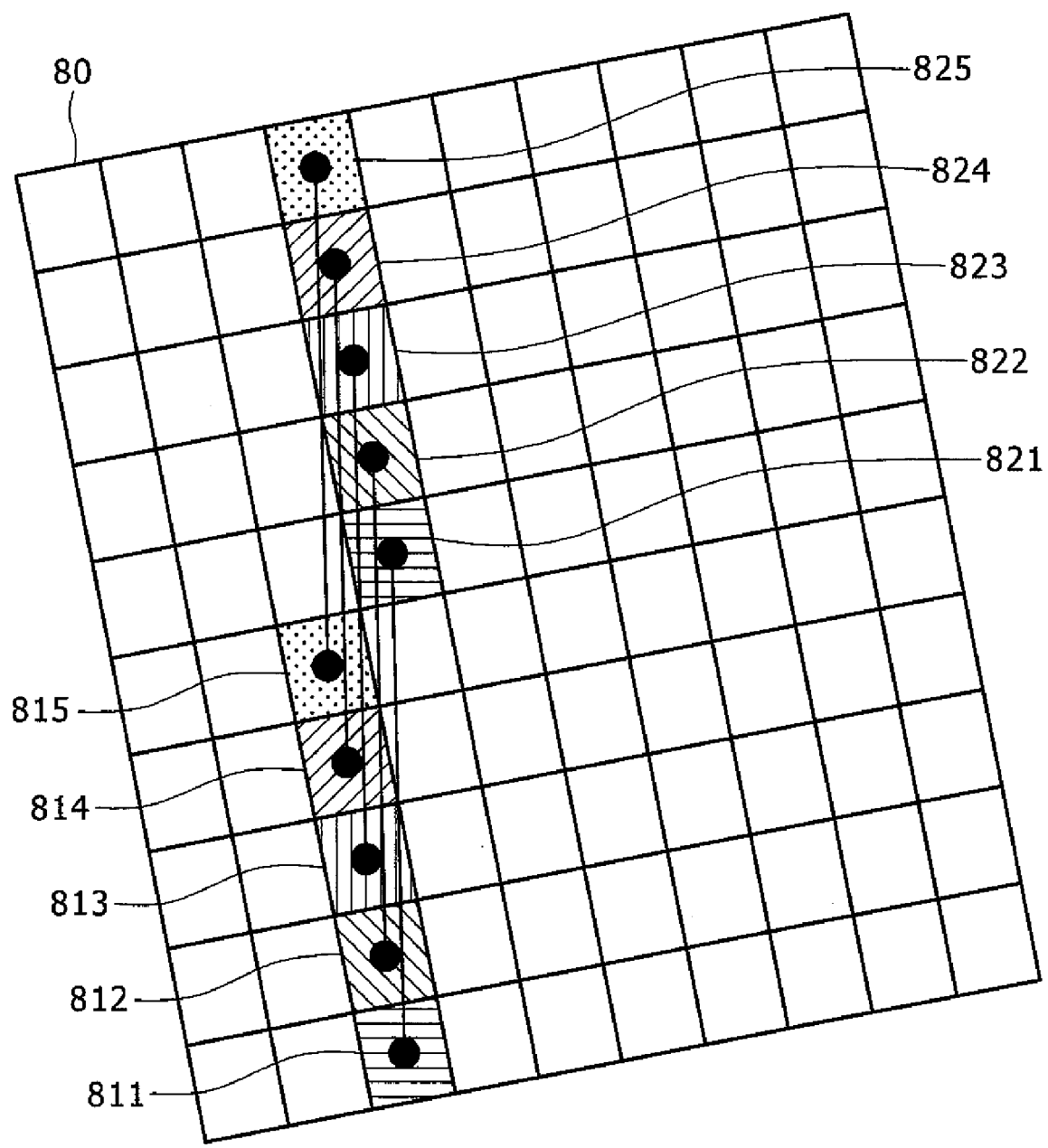
FIG. 22 shows a modification of the two-dimensional sensor.

As described above, there is a relationship of Expression (1) between the picture-element pitches ΔX and ΔY of the two-dimensional sensor 3 and the angle α. In this regard, as shown in FIG. 22, in a two-dimensional sensor 80 in which the number of picture elements is extended in the vertical direction of the two-dimensional sensor 3, the horizontal position of the (m)th picture element on the stage 1 perfectly overlaps in the vertical direction. FIG. 22 shows the case where m=5. When the stage 1 moves, each of picture elements 811 and 821, picture elements 812 and 822, picture elements 813 and 823, picture elements 814 and 824, and picture elements 815 and 825 can pick up images of the same areas on the wafer 2. Accordingly, by adding outputs of these picture elements, the image generation unit 6 generates a bright image even when a pattern on the wafer 2 is dark. As a result, an image highly contrasted with its background is obtained, which achieves highly accurate processing in defect extraction, size calculation, and defect classification.

In FIG. 22, (2×m) units of two-dimensional sensors are arranged in a direction in which the wafer moves. However, in the present embodiment, the number of the two-dimensional sensors is not limited to the above, and (3×m) units or more of the two-dimensional sensors may be arranged in the direction in which the wafer moves. In this way, the contrast of the image is improved as much as the image data is added.

In the present embodiment, the wafer 2 is irradiated by the illuminating system 4 from outside of the objective lens 5. However, a similar effect can be obtained in a structure where the wafer 2 is irradiated through the objective lens 5. Further, it is evident that even in a structure where a transparent object to be inspected such as glass through which light passes is irradiated instead of the wafer 2, the effect of the present embodiment is obtained. Further, the irradiation and detection do not necessarily have to be done by light. If the two-dimensional image pick-up is possible by a projecting optical system, the present embodiment can be adopted even when using an electronic beam.

As described above, according to the present invention, there is provided an inspection apparatus which is capable of performing highly sensitive defect extraction, highly accurate defect size measurement, and defect classification on a semiconductor wafer. Further, it can be applied to an inspection apparatus which performs detection of a defect which is smaller than the size of the detected picture element, size measurement, and classification in substrates of a printed circuit board, a hard disk, a liquid crystal, a plasma TV, an organic EL, etc. By using such apparatuses and conducting feedback to manufacturing processes, high yielding production of the above devices can be achieved.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An inspection apparatus, comprising:
   moving means capable of moving in a plane with an object to be inspected mounted thereon;
   image pick-up means for picking up an image of the object to be inspected in synchronism with the moving means; and
   image processing means which receives an output to process from the image pick-up means,
   wherein the image pick-up means includes an image sensor in which two or more linear picture-element arrays are arranged, as two-dimensional picture-element arrays, perpendicularly to a direction of the picture-element array;
   wherein a direction of the linear picture-element array of the image sensor is inclined at a predetermined angle from a direction perpendicular to a direction in which the moving means moves when the image pick-up means picks up an image of the object to be inspected; and
   wherein the image processing means processes an output from the sensor of the image pick-up means which is inclined at the predetermined angle to form an image of the object in sampling with a size less than a size of one picture-element of the two-dimensional picture-element arrays.

2. The inspection apparatus according to claim 1, wherein the image pick-up means is a CMOS sensor.

3. The inspection apparatus according to claim 1, wherein, assuming a picture-element pitch in a horizontal (line) direction of the image pick-up means is $\Delta X$, a picture-element pitch in a vertical (row) direction is $\Delta Y$, an angle made by the vertical direction and the moving direction is $\alpha$, and m is an integer, the image pick-up means is installed such that $\tan \alpha = \Delta X/(m\Delta Y)$ is substantially satisfied.

4. The inspection apparatus according to claim 1, wherein the image pick-up means includes: drive signal generation means for generating a drive signal for a picture element in synchronism with a position of the moving means; and
   a delay circuit that delays the drive signal of the picture element in the horizontal (line) direction with respect to a neighboring picture element.

5. The inspection apparatus according to claim 4, wherein the drive signal generation means generates the drive signal at intervals of a size of the picture element or less.

6. The inspection apparatus according to claim 1, wherein picture elements in the vertical (row) direction of the image pick-up means are read simultaneously.

7. The inspection apparatus according to claim 1, wherein the image processing means includes an image generation means which rearranges luminance signals of the picture elements picked up at different times and generates an image in sampling with a size less than size of the picture element.

8. The inspection apparatus according to claim 1, wherein the image generation means adds two or more of the picture elements in a vertical (row) direction of the image pick-up means in the moving direction of the moving means.

9. An inspection apparatus, comprising:
   moving means capable of moving in a plane with an object to be inspected mounted thereon;
   image pick-up means for picking up an image of the object to be inspected in synchronism with the movement of the moving means, and
   image processing means which receives an output to process from the image pick-up means,
   wherein the image pick-up means is divided into a first to (m)th lines for each $\Delta Y$ in a y-direction and a first to (n)th rows for each $\Delta X$ in an x-direction, and picture elements having a size of $\Delta X \times \Delta Y$ are arranged two-dimensionally;
   wherein the moving means moves the mounted object to be inspected from the first line to the (m)th line of the image pick-up means in a direction inclined at a predetermined angle $\alpha$ to the y-direction, and an image of the object to be inspected is picked up at each of the first to (m)th lines as the object to be inspected moves toward a first direction; and
   wherein the image processing means processes an output from the sensor of the image pick-up means which is inclined at the predetermined angle to form an image of the object in sampling with a size less than a size of one picture-element of the two-dimensional picture-element arrays.

10. The inspection apparatus according to claim 9, wherein the predetermined angle $\alpha$ satisfies: $\tan \alpha = \Delta X/(m\Delta Y)$.

11. The inspection apparatus according to claim 10, wherein, assuming a moving speed of the object to be inspected is V and p is an integer equal to or larger than 1 and smaller than n in the image pick-up means, an image pick-up time of a (p+1)th row in the same line is delayed by $\Delta X \sin \alpha / V$ from an image pick-up time of a (p)th row.

12. The inspection apparatus according to claim 9, wherein the image pick-up means picks up images of the object to be inspected two or more times while the object to be inspected moves toward the first direction by $\Delta Y$.

13. An inspection apparatus, comprising:
   moving means capable of moving in a plane with an object to be inspected mounted thereon;
   image pick-up means for picking up an image of the object to be inspected in synchronism with the moving means,
   image processing means which receives an output to process from the image pick-up means,
   wherein the image pick-up means is divided into a first to (q×m)th lines for each $\Delta Y$ in a y-direction and a first to (n)th rows for each $\Delta X$ in an x-direction, picture elements having a size of $\Delta X \times \Delta Y$ are arranged two dimensionally, and m, n, and q are integers;
   wherein the object to be inspected moves from the first line to the (m)th line of the image pick-up means in a direction inclined at a predetermined angle to the y-direction;
   wherein an image of the object to be inspected is picked up at each of the first to (m)th lines as the object to be inspected moves in a first direction;
   wherein data of the picked up image is added for each the (m)th line
   wherein the image processing means processes an output from the sensor of the image pick-up means which is inclined at the predetermined angle to form an image of the object in sampling with a size less than a size of one picture-element of the two-dimensional picture-element arrays.

14. The apparatus for inspection according to claim 13, wherein the q is 2.

15. A method of inspection, comprising the steps of:
   mounting an object to be inspected on moving means and moving the object to be inspected in a plane;

picking up images of the object to be inspected in synchronism with the moving means, and processing image by receiving an output to process from the image pick-up means, wherein images of the object to be inspected are picked up in the step of picking up images with use of image pick-up means in which two or more linear picture-element arrays are arranged, as two-dimensional picture-element arrays, in a direction perpendicular to a direction of the picture-element array while the object to be inspected is moved being inclined at a predetermined angle to a direction of the picture-element array of the image pick-up means; and wherein in the step of processing image, processing an output from the sensor of the image pick-up means which is inclined at the predetermined angle to form an image of the object in sampling with a size less than a size of one picture-element of the two-dimensional picture-element arrays.

16. The method of inspection according to claim 15, wherein the image pick-up means is a CMOS sensor.

17. The method of inspection according to claim 15, wherein, assuming a picture-element pitch in a horizontal (line) direction (a direction of the linear picture-element arrays) of the image pick-up means is $\Delta X$, a picture-element pitch in a vertical (row) direction (a direction perpendicular to the linear picture-element arrays) is $\Delta Y$, an angle made by the vertical direction and the moving direction is $\alpha$, and m is an integer, an image of the object to be inspected is picked up such that the image pick-up means is installed so as to substantially satisfy $\tan \alpha = \Delta X/(m\Delta Y)$ in the step of picking up images.

18. The method of inspection according to claim 15, wherein a drive signal for picture elements is generated in synchronism with a position of the moving means and the drive signal for picture elements in the horizontal (line) direction is delayed with respect to a neighboring picture element in the step of picking up images.

19. The method of inspection according to claim 18, wherein drive signals for the picture elements are generated at intervals of the picture-element size or less.

20. The method of inspection according to claim 15, wherein picture elements in the vertical (row) direction of the image pick-up means are read simultaneously in the step of picking up images.

21. The method of inspection according to claim 15 wherein the step of processing the image including a step of generating an image, wherein luminance signals of the picture elements picked up at different times are rearranged and the image is generated in sampling with a size less than the picture-element size in the step of generating the image.

22. The method of inspection according to claim 15, wherein the image pick-up means is an image sensor of a time-delay integral type.

* * * * *